United States Patent [19]
Cox

[11] Patent Number: 5,820,629
[45] Date of Patent: Oct. 13, 1998

[54] INTIMAL LINING TRANSITION DEVICE AND ENDARTERECTOMY METHOD

[75] Inventor: Brian J. Cox, Cupertino, Calif.

[73] Assignee: Medtronic, Inc., Minneapolis, Minn.

[21] Appl. No.: 696,130

[22] Filed: Aug. 13, 1996

[51] Int. Cl.⁶ .......................... A61B 17/22; A61B 17/36; A61B 19/00
[52] U.S. Cl. ............................. 606/159; 128/898; 606/47
[58] Field of Search ................................ 606/1, 159, 167, 606/170, 171, 32, 37, 39, 40, 45–52

[56] References Cited

U.S. PATENT DOCUMENTS

| | | |
|---|---|---|
| 1,167,014 | 1/1916 | O'Brien . |
| 2,944,552 | 7/1960 | Cannon ................................. 606/159 |
| 3,564,582 | 2/1971 | Tjong-Joe-Wai . |
| 3,837,345 | 9/1974 | Matar . |
| 4,665,918 | 5/1987 | Garza et al. . |
| 4,765,332 | 8/1988 | Fischell et al. . |
| 4,994,067 | 2/1991 | Summers . |
| 5,100,423 | 3/1992 | Fearnot ................................. 606/159 |
| 5,366,463 | 11/1994 | Ryan . |
| 5,409,454 | 4/1995 | Fischell et al. . |
| 5,480,379 | 1/1996 | LaRosa ................................. 606/159 |

FOREIGN PATENT DOCUMENTS

| | | |
|---|---|---|
| 0119688 | 9/1984 | European Pat. Off. . |
| 0274846 | 7/1988 | European Pat. Off. . |
| 2635962 | 3/1990 | France . |
| WP 90/01969 | 3/1990 | WIPO . |
| WO 94/04096 | 3/1994 | WIPO . |

OTHER PUBLICATIONS

G. Ho et al., "The mollring cutter™ remote endarterectomy: preliminary experience with a new endovascular technique for treatment of occlusive superficial femoral artery disease," *Journal of Endovascular Surgery*, 2(3) :278 (Aug., 1995).

H. Joosten et al., "The mollring cutter™ remote endarterectomy," *Clinical Ischaemia*, 6(1) :14 (in existence as of May 30, 1996).

Remote endarterectomy using the ring strip cutter technique (in existence as of May 31, 1996).

*Primary Examiner*—Glenn K. Dawson
*Attorney, Agent, or Firm*—Townsend and Townsend and Crew LLP

[57] ABSTRACT

A device (24) for creating a smooth transition in the intimal lining (18) of a blood vessel (16) during an endarterectomy procedure on a patient (2) includes a delivery catheter (28) insertable into the blood vessel at an opening (8) in the blood vessel. An intimal lining cutter (38, 56) is disposed at the distal end (30) of the catheter. When in proper position, that is where the intimal lining separates from the vessel wall (20), the cutter is actuated to cut the intimal lining without leaving a flap of intimal lining within the blood vessel. The cutter can be of different types, including electrocautery coil (38) or a radially extending cutter blade (56). The invention is typically used with a ring stripper (14) and permits the endarterectomy to be performed using only a single incision into the vessel.

18 Claims, 4 Drawing Sheets

INTIMAL LINING TRANSITION DEVICE AND ENDARTERECTOMY METHOD

CROSS REFERENCE TO RELATED APPLICATIONS

This invention is related to PCT/NL94/00254 for AN INSTRUMENT FOR LOOSENING AND CUTTING THROUGH THE INTIMA OF A BLOOD VESSEL, AND A METHOD THEREFOR, filed Oct. 18, 1994, published May 4, 1995 as Publication No. WO 95/11633, and PCT/NL95/00336 for ASSEMBLY FOR TREATING BLOOD VESSELS AND METHODS THEREFOR, filed Oct. 4, 1995, published as Publication No. WO 9610375-A1, the disclosures of which are incorporated by reference.

BACKGROUND OF THE INVENTION

This invention relates to a device or assembly for the treating of blood vessels and more specifically to a device or assembly for creating a smooth transition in the intimal lining of a blood vessel after an endarterectomy and to an endarterectomy method using the device.

An often occurring medical problem is the deposition on the inner walls of blood vessels with for instance calcium, so-called arteriosclerosis. Because of this, a blockage of the blood vessel occurs, so-called stenosis.

Stenosis of blood vessels which leads to a narrowing and, in some cases, complete blocking of the blood vessel can lead to dangerous consequences for the patient. A blood vessel which is particularly susceptible to stenosis is the femoral artery between the groin and the knee. Circulatory problems and a deterioration in health can ensue. Advanced stenosis, if not operated upon, can cause wastage and death of body tissue, necessitating, in certain instances, in amputation.

A known procedure for unblocking blood vessels, endarterectomy, is to separate the inner layer of the blood vessel, the so called tunica-intima or intimal lining, from the blood vessel wall using a ring stripper, to cut through and sever the intimal lining over the blocked length of the blood vessel from within the blood vessel and then to remove the intimal lining plus blockage from the body. A new intimal lining then grows back to replace this removed intimal lining.

A problem with this procedure is that the original intimal lining is usually separated from the blood vessel wall up to a distance just past where it is to be severed. Hence on removal of the original intimal lining, a small piece or flap of the intimal lining is left hanging loosely in the blood stream. The flap may be a site for flow stagnation and thrombosis; the site may be a particular problem if the tissue flap faces upstream so that it catches the blood flow. While the distal tissue flap has been successfully held open by deployment of a stent inside the vessel to cover the flap, vascular stents have their own disadvantages, such as reduced flexibility of the vessel. In addition, stents are expensive medical devices.

SUMMARY OF THE INVENTION

This invention is directed to a device and method for creating a smooth transition in the intimal lining of a blood vessel during an endarterectomy procedure. The invention creates a smooth transition by separating the intimal lining from the remainder of the blood vessel at the distal end of the separated intimal lining, that is, where the intimal lining separates from the remainder of the blood vessel.

The intimal lining transition device is preferably used with an intimal lining separation tool, typically a ring stripper. The ring stripper is introduced into the blood vessel a start position and extends down through the blood vessel; doing so separates the tubular intimal lining from the vessel wall of the blood vessel from the start position to an end position.

The intimal lining transition device includes a distal end insertable into a blood vessel at the start position. The distal end is positioned at the end position, that is at the distal end of the separated intimal lining; this location is called the separation region. A user actuated intimal lining cutter is located at the distal end of the transition device. Upon actuation by the user, the intimal lining cutter severs the separated intimal lining from the remainder of the blood vessel. The separated intimal lining can be removed from the patient while leaving the blood vessel is free from any flap of intimal lining at the separation region.

The intimal lining cutter can be of different types, including an electrocautery coil, which uses cauterization to sever the separated intimal lining from the remainder of the blood vessel, or a radially extendable blade.

The primary advantage of the invention is that it permits the endarterectomy procedure to be conducted using only a single entry point into the blood vessel. This reduces patient trauma and the number of possible infection sites. The invention can be practiced with conventional ring strippers which are well known instruments, relatively inexpensive and can be reused. The resulting transition between the stripped region of the blood vessel and the unstripped region is smooth to help prevent the creation of a site for restenosis of the blood vessel, as can be created when a flap of intimal lining remains after a conventional endarterectomy procedure.

Other features and advantages of the invention will appear from the following description in which the preferred embodiments have been set forth in detail in conjunction with the accompanying drawings.

BRIEF DESCRIPTION OF THE DRAWINGS

FIGS. 5, 6 and 7 are three different embodiments of electrocautery coils while

DESCRIPTION OF THE PREFERRED EMBODIMENTS

Figure 1:
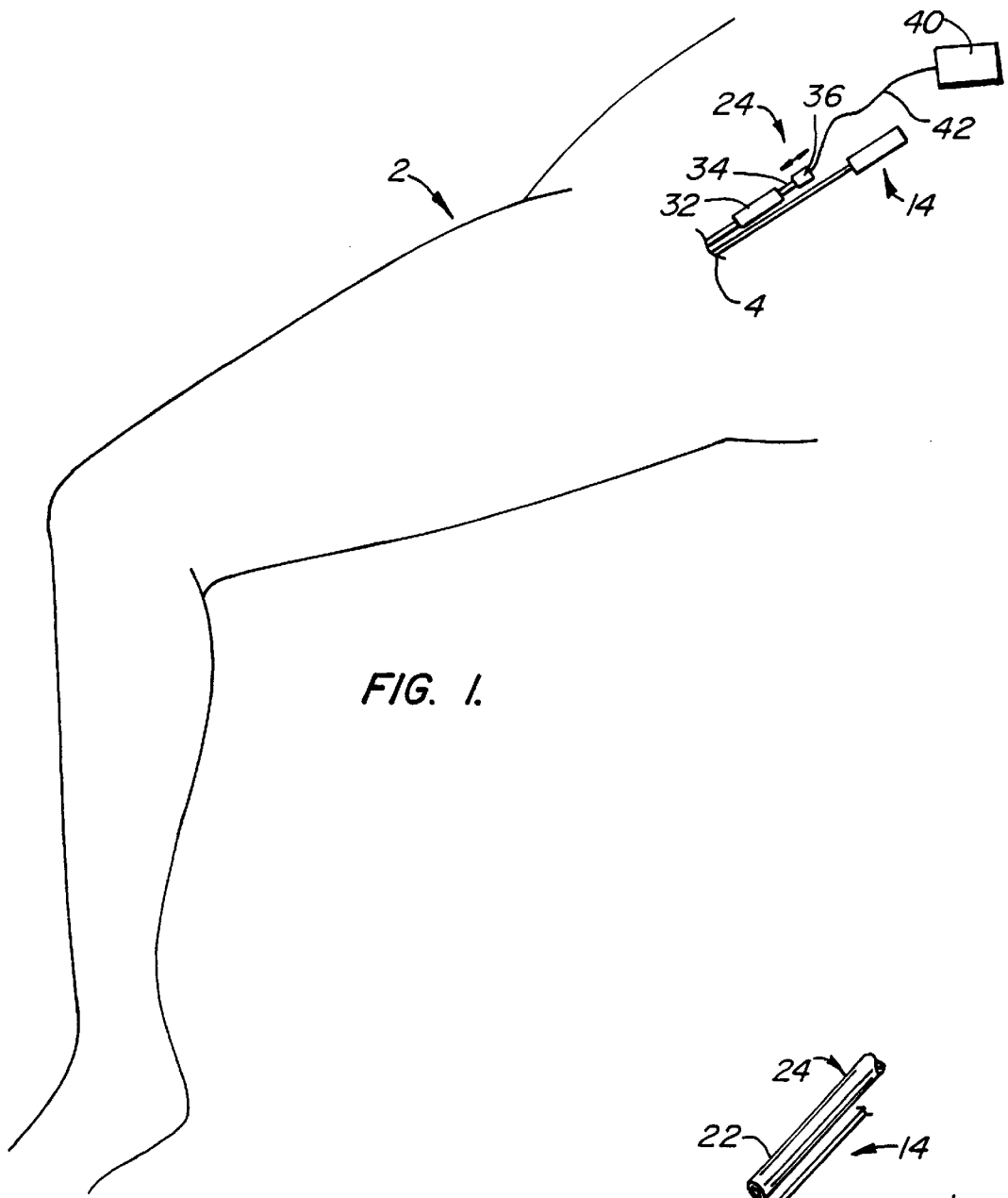
FIG. 1 is a simplified view showing the leg of a patient with a ring stripper and a transition device made according to the invention inserted into the femoral artery of the patient through an incision.
Figure 2:
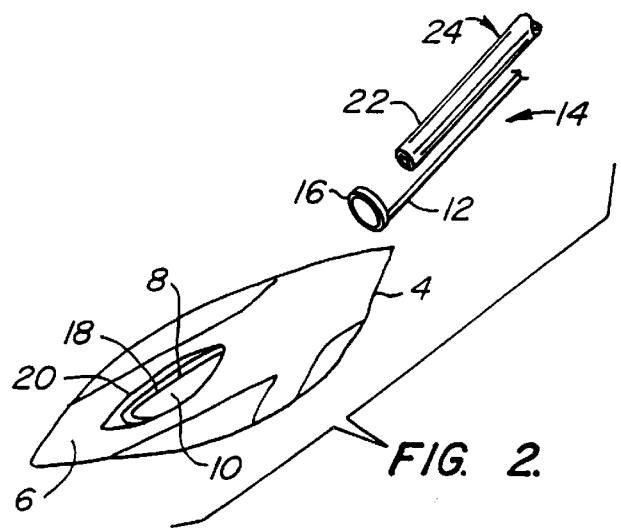
FIG. 2 is a simplified, enlarged view, showing the incision of FIG. 1, the exposed femoral artery having an opening for the introduction of the distal ends of the ring stripper transition device of FIG. 1.

FIG. 1 illustrates the leg of a patient 2, in which an incision 4 has been made to gain access to the femoral artery 6, see FIG. 2, and an opening 8 made in artery 6 to provide access to the interior 10 of the artery. The distal end 12 of a conventional ring stripper 14 includes a cutter ring 16 which is passed into artery 6 between the intimal lining or layer 18 of artery 6 and the vessel wall 20 of the artery. Ring stripper 14 has a handle 21 at its proximal end. The intimal lining 18 and the vessel wall 20 are shown in more detail in FIG. 3. The distal end 22 of an intimal lining transition device 24 is passed through opening 8 into interior 10 after the introduction of cutter ring 16 into artery 6.

Figure 3:
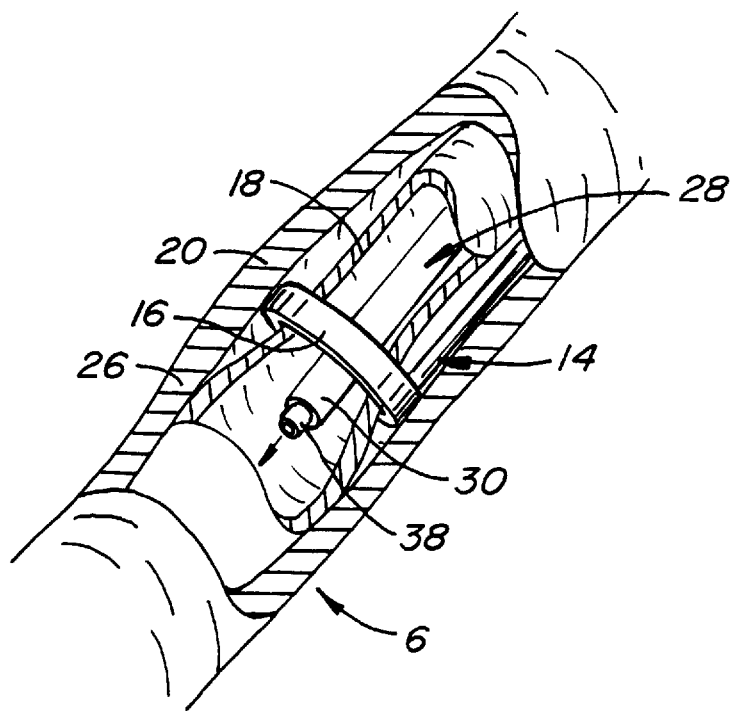
FIG. 3 is an enlarged view showing the ring stripper and transition device where the transition device has separated the intimal lining from the wall of the blood vessel.
Figure 4:
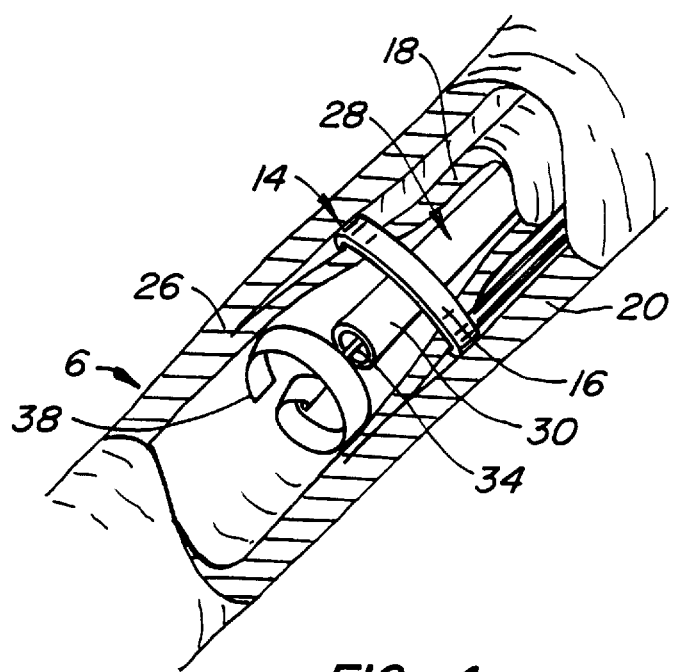
FIG. 4 is similar to FIG. 3 but shows the deployment of an electrocautery coil from a delivery catheter of the transition device at the separation region at the distal end of the separated intimal lining.

FIG. 3 illustrates ring stripper 14 and transition device 24 in their distal, deployed positions. This is typically about 20 to 40 cm from incision 4. While the cutter ring 16 of ring stripper 14 has separated tubular intimal lining 18 from vessel wall 20 of artery 6, intimal lining 18 must still be severed at the distal end of the separated intimal lining so that the separated intimal lining and the blockage within the intimal lining can be pulled out through opening 8 and incision 4. To ensure that substantially no flap of intimal lining 18 remains, it is necessary to cut or sever intimal lining 18 at the separation region 26 at which intimal lining 18 separates from wall 20, that is where intimal lining 18 separates from the remainder of artery 6. This is achieved using transition device 24.

Transition device 24 includes a hollow delivery catheter 28 having an open distal end 30 and being connected to a handle 32 at its proximal end. Delivery catheter 28 houses an elongate manipulator wire 34 which slides within delivery catheter. Manipulator wire 34 is connected at its proximal end to a longitudinal positioner 36 and carries an electrocautery coil 38 at its distal end.

Electrocautery coil 38 is initially positioned within distal end 30 of delivery catheter 28. When coil 38 is to be deployed at separation region 26, manipulator wire 34 is pushed distally through the use of positioner 36. Doing so allows electrocautery coil 38 to escape from distal end 30 and, due to its inherent resiliency, to press against intimal lining 18 at separation region 26. Energy is then applied to electrocautery coil 38 by manipulator wire 34; manipulator wire 34 acts as an insulated electrical conductor extending from coil 38 to positioner 36. Positioner 36 is coupled to a power source 40 by a wire 42. The electrical path provided by manipulator wire 34 could also be provided by a separate electrical conductor.

Figure 5:
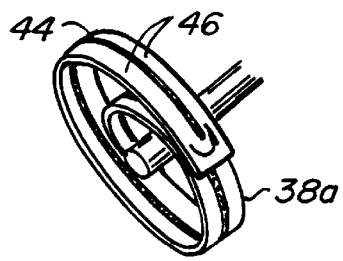
Figure 6:
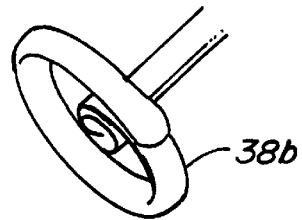
Figure 5A:
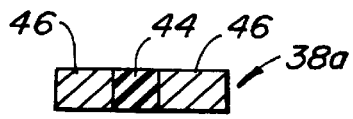
FIGS. 5A, 6A and 7A are cross-sectional views of the respective coils.
Figure 6A:
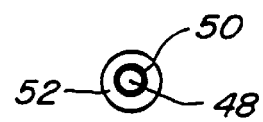

FIGS. 5 and 5A illustrate a first electrocautery coil 38a in which the body of the coil comprises a center insulator 44 and electrical conductors 46 on either side of the insulator. FIGS. 6 and 6A illustrate the second embodiment of coil 38b in which the coil is a coaxial coil having an electrically conductive core 48, a non-conductive layer 50 surrounding core 48 and a conductive layer 52 surrounding layer 50. In both cases, the electrical conductors 46 and 48, 52 are connected at the distal ends of coils 38a, 38b. Other configurations are also possible.

Figure 7:
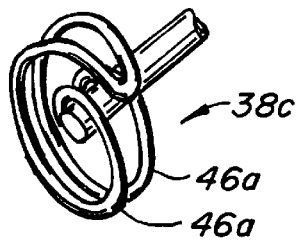
Figure 7A:
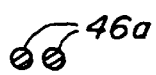

FIGS. 7 and 7A illustrate a further embodiment of the invention in which a coil 38c comprises a pair of spaced-apart conductors 46a joined at their distal ends which act in a manner similar to the embodiment of FIGS. 5 and 5A. If desired, insulating spacers may be used between the parallel runs of conductors 46a to help avoid short circuits; portions of wires 46a facing one another could be insulated for the same reason.

Figure 8:
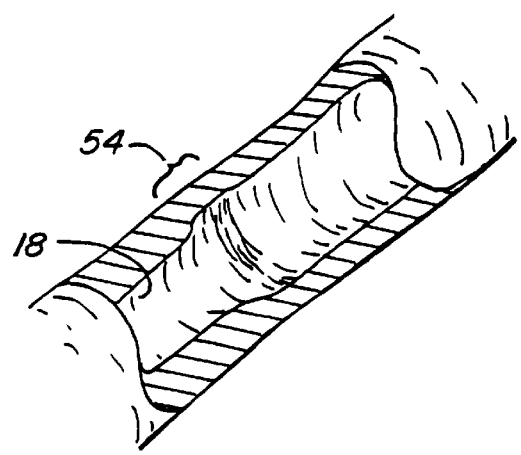
FIG. 8 illustrates the blood vessel after the electrocautery coil has been sufficiently energized to cut or separate the distal end of the separated intimal lining from the remainder of the blood vessel providing a smooth transition region free of a flap of intimal lining, and after the separated intimal lining has been removed through the opening and incision of FIG. 2 along with the ring stripper and transition device.

FIG. 8 illustrates the results of separating or cutting intimal lining 18 at separation region 26 and then the removal of ring stripper 14 and the separated tubular intimal lining 18. It can be seen that transition region 54 is substantially free of a flap of intimal lining 18 which could otherwise be present if, for example, intimal lining 18 were severed at the position of cutter ring 16 in FIG. 3.

In use, incision 4 and opening 8 are made in patient 2 to provide access to the interior 10 of artery 6. Ring stripper 14 is then introduced into artery 6 with cutter ring 16 positioned between intimal lining 18 and vessel wall 20. After cover ring 16 has extended about 20 to 40 cm, distal end 22 of transition device 24 is inserted into interior 10 of artery 6. After ring stripper 14 has separated a sufficient length of intimal lining 18 away from vessel wall 20, distal end 30 is positioned generally opposite separation region 26. Electrocautery coil 38 is then extended from distal end 30 to automatically engage intimal lining 18 at separation region 26.

The proper positioning of electrocautery coil 38 can be achieved in a number of different ways. For example, distal end 30 of delivery catheter 28 and one or both of electrocautery coil 38 and the distal end of manipulator wire 34, can include radiopaque material. Also, the relative positions of handles 21, 32 can be used to help determine the proper positioning of electrocautery coil 38. Once in proper position, power source 40 is used to provide sufficient energy to electrocautery coil 38 to cut or sever intimal lining 18 from vessel wall 20 at separation region 26. The separated intimal lining 18 can then be withdrawn from artery 6 simultaneously with ring stripper 14 and transition device 24. Appropriate medical procedures, such as suturing, are then conducted to close opening 8 and incision 4.

Figure 9:
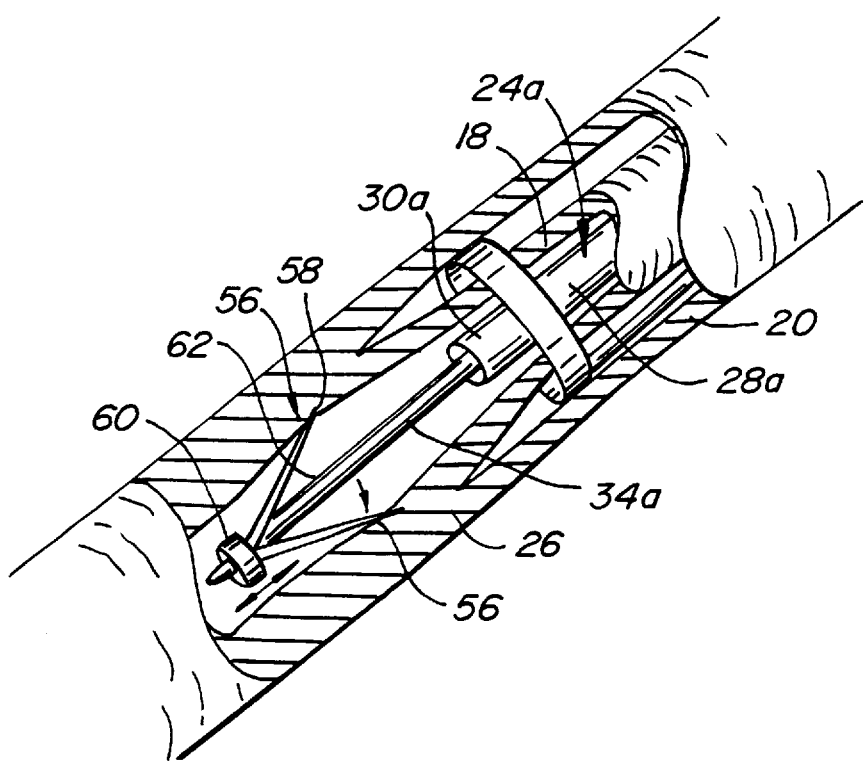
FIG. 9 illustrates an alternative embodiment of the invention in which the electrocautery coil cutting element has been replaced by radially extending cutting blades shown in the extended or deployed position at the separation region at the end of the separated intimal lining.

FIG. 9 illustrates an alternative embodiment of the invention in which a transition device 24a is used instead of transition device 24. Transition device 24a is similar to transition device 24 in that it includes a delivery catheter 28 housing a manipulator wire 34a and a pull wire 62 extending from a pair of handles, not shown. Instead of electrocautery coil 38, a set of generally radially extending blades 56 are used. Blades 56 have cutting edges 58 at their distal ends. Blades 56 extend radially outwardly and longitudinally proximally from the distal end of manipulator wire 34. Blades 56 are normally housed within distal end 30a of delivery catheter 28a. Once intimal lining 18 has been fully separated from vessel wall 20, distal end 30a is positioned axially adjacent separation region 26. Manipulator wire 34a is pushed distally to permit blades 56 to emerge from within delivery catheter 56a to the position of FIG. 8. The natural outward bias of blades 56 causes them to engage intimal lining 18 at separation region 26. Blades 56 are then rotated and pulled proximally by the user manipulating the handle (not shown) at the proximal end of manipulator wire 34a. The radial outward movement of blades 56 is preferably limited so as not to pass through vessel wall 20. Blades 56 cut through intimal lining so to eliminate any flap of intimal lining and create a smooth transition region as shown in FIG. 7. After the cut is made, pull wire 62, which is connected to blade retaining ring 60, is pulled by the user to cause the retaining ring to slide over blades 56, thus folding them against manipulator wire 34a so that the blades can be returned to within distal end 30*a* of delivery catheter 28*a*. Transition device 24*a*, ring stripper 14 and the severed intimal lining 18 are then removed from the patient.

Other modifications and variations can be made to the disclosed embodiments without departing from the subject of the invention as defined in the following claims. For example, blades 56 could extend completely radially as opposed to both radially and longitudinally as in the preferred embodiment. Delivery catheter 28 could include only a tubular distal portion at the distal end of a positioning wire.

What is claimed is:

1. A device for creating a smooth transition in the intimal lining of a blood vessel during an endarterectomy procedure on a patient comprising:

a transition device having a distal end insertable into a vessel to an intimal lining separation region at which an intimal lining of the blood vessel separates from the vessel wall of the blood vessel, the transition device comprising:

an elongate, user-actuated manipulator element with a distal end; and the distal end comprising a user-actuated, flapless intimal lining cutter positionable at the separation region and constructed to permit a user to energize the intimal lining cutter to cut the intimal lining at the separation region so that when a length of the intimal lining proximal of the separation region is removed from a patient, the blood vessel has a smooth transition and is free from a flap of intimal lining at the separation region, the intimal lining cutter comprising a coiled, axially-aligned electrocauterizing element mounted to the distal end of the manipulator element.

2. The device according to claim 1 wherein the transition device comprises a delivery element having a tubular distal portion housing the intimal lining cutter while said intimal lining cutter passes through the vessel.

3. The device according to claim 2 wherein the entire delivery element comprises a tubular element.

4. The device according to claim 2 wherein the intimal lining cutter comprises a radially-movable cutter movable from a radially-contracted condition when housed within the tubular distal portion to a radially-expanded condition when released from the tubular distal portion to engage the intimal lining at the separation region.

5. A method of removing a length of the intimal lining of a blood vessel comprising the following steps:

inserting an intimal lining separation tool into the interior of a blood vessel at a start position;

separating, using the tool, a length of intimal lining from a vessel wall of the blood vessel from the start position to an end position;

flaplessly severing, from within the blood vessel, the separated length of intimal lining at the end position using a transition device extending from the end position, through the blood vessel interior and out of the blood vessel at the start position, so as to leave a smooth transition and substantially no flap of intimal lining at the end position; and removing the separated length of intimal lining from the blood vessel.

6. The method according to claim 5 wherein the tool-inserting step is carried out using a femoral artery as the blood vessel.

7. The method according to claim 5 wherein the tool-inserting step is carried out using a ring stripper as the intimal lining separation tool.

8. The method according to claim 5 wherein the tool-inserting step comprises the step of making an incision in the blood vessel at the start position.

9. The method according to claim 5 wherein the severing step is carried out using a radially extendable blade.

10. The method according to claim 9 wherein the severing step includes the steps of:

positioning the blade, while in a retracted condition, at the end position;

extending the blade to an extended, cutting condition; and moving the blade so as to cut the intimal lining at the end position.

11. The method according to claim 10 wherein the positioning step further comprises the step of housing the blade in the retracted condition within a tubular portion of a delivery element, said delivery element passing from the start position and through the blood vessel.

12. The method according to claim 11 wherein the extending step is carried out by removing the radially extendable blade from the tubular portion.

13. The method according to claim 10 wherein the blade moving step is carried out by rotating the blade about an axis of the blood vessel.

14. A method of removing a length of the intimal lining of a blood vessel comprising the following steps:

inserting an intimal lining separation tool into the interior of a blood vessel at a start position;

separating, using the tool, a length of the intimal lining from the blood vessel from the start position to an end position;

using an electrocautery element to flaplessly sever the separated length of intimal lining at the end position from within the blood vessel to leave substantially no flap of intimal lining; and removing the separated length of intimal lining from the blood vessel.

15. The method according to claim 14 wherein the severing step is carried out by positioning the electrocautery element against the intimal lining at the end position and applying energy to the electrocautery element.

16. The method according to claim 14 wherein the severing step comprises the step of:

positioning the electrocautery element, while in a constrained condition, at the end position;

expanding the electrocautery element to contact the intimal lining at the end position; and applying sufficient power to the electrocautery element to separate said length of intimal lining from said blood vessel.

17. The method according to claim 16 wherein said positioning step is carried out by initially housing the electrocautery element coiled within a tubular portion of a delivery element, said delivery element passing through the blood vessel.

18. The method according to claim 17 wherein said expanding step includes the step of removing the electrocautery element from said tubular portion.

* * * * *